(12) United States Patent
Patek et al.

(10) Patent No.: US 7,585,959 B2
(45) Date of Patent: Sep. 8, 2009

(54) FEEDBACK RESISTANT ACETOHYDROXY ACID SYNTHETHASE MUTANTS

(75) Inventors: Miroslav Patek, Prague (CZ); Veronika Elisakova, Prague (CZ)

(73) Assignee: Evonik Degussa GmbH, Essen (DE)

(*) Notice: Subject to any disclaimer, the term of this patent is extended or adjusted under 35 U.S.C. 154(b) by 351 days.

(21) Appl. No.: 10/561,906

(22) PCT Filed: Jun. 8, 2004

(86) PCT No.: PCT/EP2004/006157

§ 371 (c)(1),
(2), (4) Date: Dec. 21, 2005

(87) PCT Pub. No.: WO2005/003357

PCT Pub. Date: Jan. 13, 2005

(65) Prior Publication Data

US 2007/0292914 A1    Dec. 20, 2007

(30) Foreign Application Priority Data

Jun. 26, 2003    (EP) .................................. 03014640

(51) Int. Cl.
C07H 21/04    (2006.01)
C07K 14/00    (2006.01)
C12N 15/09    (2006.01)

(52) U.S. Cl. ...................... 536/23.2; 530/300; 435/69.1

(58) Field of Classification Search ........................ None
See application file for complete search history.

(56) References Cited

U.S. PATENT DOCUMENTS

2002/0037562 A1*   3/2002   Livshits et al. .............. 435/136
2002/0197605 A1*  12/2002   Nakagawa et al. ............. 435/6

FOREIGN PATENT DOCUMENTS

| EP | 0 356 739 | 3/1990 |
| EP | 1 108 790 | 6/2001 |
| WO | 02/31158  | 4/2002 |

OTHER PUBLICATIONS

Kopecky et al., "Mutations in two distinct regions of Acetolactate Synthase Regulatory Subunit from Streptomyces cinnamonensis result in the lack of sensitivity to end-product inhibition", Biochemical and Biophysical Research Communications 226: 162-166 (1999).*

* cited by examiner

*Primary Examiner*—Anand U Desai
(74) *Attorney, Agent, or Firm*—Oblon, Spivak, McClelland, Maier & Neustadt, P.C.

(57) ABSTRACT

The present invention provides nucleotide sequences coding for acetohydroxy acid synthetase (AHAS) mutants, the mutated enzymes themselves and a process for the fermentative production of branched-chain amino acids using these enzymes in specific hosts in which genes which code for the modified acetohydroxy acid synthetase (AHAS) are expressed.

16 Claims, 2 Drawing Sheets

```
                        SEQUENCE LISTING

<160> NUMBER OF SEQ ID NOS: 12

<210> SEQ ID NO 1
<211> LENGTH: 519
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(519)

<400> SEQUENCE: 1
```

```
atg gtc aat tct gac gtc acc cgc cac atc ctg tcc gta ctc gtt cag        48
Met Val Asn Ser Asp Val Thr Arg His Ile Leu Ser Val Leu Val Gln
1               5                   10                  15 gac gta gac gat gac ttt tcc cgc gta tca ggt atg ttc acc cga cgc        96
Asp Val Asp Asp Asp Phe Ser Arg Val Ser Gly Met Phe Thr Arg Arg
            20                  25                  30 gca ttc aac ctc gtg tcc ctc gtg tct gca aag acc gaa aca cac ggc       144
Ala Phe Asn Leu Val Ser Leu Val Ser Ala Lys Thr Glu Thr His Gly
        35                  40                  45 atc aac cgc atc acg gtt gtt gtc gac gcc gac gag ctc aac att gag       192
Ile Asn Arg Ile Thr Val Val Val Asp Ala Asp Glu Leu Asn Ile Glu
50                  55                  60 cag atc aac aag cag ctc aac aag ctg atc ccc gtg ctc aaa gtc gtg       240
Gln Ile Asn Lys Gln Leu Asn Lys Leu Ile Pro Val Leu Lys Val Val
65                  70                  75                  80 cga ctt gat gaa gag acc act atc gcc cgc gca atc atg ctg gtt aag       288
Arg Leu Asp Glu Glu Thr Thr Ile Ala Arg Ala Ile Met Leu Val Lys
                85                  90                  95 gtc tct gcg gac agc acc aac cgt ccg cag atc gtc gac gcc gcg aac       336
Val Ser Ala Asp Ser Thr Asn Arg Pro Gln Ile Val Asp Ala Ala Asn
            100                 105                 110 atc ttc cgc gcc cga gtc gtc gac gtg gct cca gac tct gtg gtt att       384
Ile Phe Arg Ala Arg Val Val Asp Val Ala Pro Asp Ser Val Val Ile
        115                 120                 125 gaa tcc aca ggc acc cca ggc aag ctc cgc gca ctg ctt gac gtg atg       432
Glu Ser Thr Gly Thr Pro Gly Lys Leu Arg Ala Leu Leu Asp Val Met
130                 135                 140 gaa caa ttc gaa atc cgc gaa ctg atc caa tcc gga cag att gca ctc       480
Glu Gln Phe Glu Ile Arg Glu Leu Ile Gln Ser Gly Gln Ile Ala Leu
145                 150                 155                 160 aac cgc ggt ccg aag acc atg gct ccg gcc aag atc taa                   519
Asn Arg Gly Pro Lys Thr Met Ala Pro Ala Lys Ile
                165                 170
```

<210> SEQ ID NO 2
<211> LENGTH: 172
<212> TYPE: PRT
<213> ORGANISM: Artificial Sequence
<220> FEATURE:
<223> OTHER INFORMATION: Synthetic Construct

<400> SEQUENCE: 2

```
Met Val Asn Ser Asp Val Thr Arg His Ile Leu Ser Val Leu Val Gln
1               5                   10                  15

Asp Val Asp Asp Asp Phe Ser Arg Val Ser Gly Met Phe Thr Arg Arg
            20                  25                  30

Ala Phe Asn Leu Val Ser Leu Val Ser Ala Lys Thr Glu Thr His Gly
        35                  40                  45

Ile Asn Arg Ile Thr Val Val Val Asp Ala Asp Glu Leu Asn Ile Glu
    50                  55                  60

Gln Ile Asn Lys Gln Leu Asn Lys Leu Ile Pro Val Leu Lys Val Val
65                  70                  75                  80

Arg Leu Asp Glu Glu Thr Thr Ile Ala Arg Ala Ile Met Leu Val Lys
                85                  90                  95

Val Ser Ala Asp Ser Thr Asn Arg Pro Gln Ile Val Asp Ala Ala Asn
            100                 105                 110

Ile Phe Arg Ala Arg Val Val Asp Val Ala Pro Asp Ser Val Val Ile
        115                 120                 125
```

```
Glu Ser Thr Gly Thr Pro Gly Lys Leu Arg Ala Leu Leu Asp Val Met
    130                 135                 140

Glu Gln Phe Glu Ile Arg Glu Leu Ile Gln Ser Gly Gln Ile Ala Leu
145                 150                 155                 160

Asn Arg Gly Pro Lys Thr Met Ala Pro Ala Lys Ile
                165                 170

<210> SEQ ID NO 3
<211> LENGTH: 519
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(519)

<400> SEQUENCE: 3 atg gct aat tct gac gtc acc cgc cac atc ctg tcc gta ctc gtt cag     48
Met Ala Asn Ser Asp Val Thr Arg His Ile Leu Ser Val Leu Val Gln
1               5                   10                  15 gac gta gac ggt gac ttt tcc cgc gta tca ggt atg ttc acc cga cgc     96
Asp Val Asp Gly Asp Phe Ser Arg Val Ser Gly Met Phe Thr Arg Arg
            20                  25                  30 gca ttc aac ctc gtg tcc ctc gtg tct gca aag acc gaa aca cac ggc    144
Ala Phe Asn Leu Val Ser Leu Val Ser Ala Lys Thr Glu Thr His Gly
        35                  40                  45 atc aac cgc atc acg gtt gtt gtc gac gcc gac gag ctc aac att gag    192
Ile Asn Arg Ile Thr Val Val Val Asp Ala Asp Glu Leu Asn Ile Glu
    50                  55                  60 cag atc acc aag cag ctc aac aag ctg atc ccc gtg ctc aaa gtc gtg    240
Gln Ile Thr Lys Gln Leu Asn Lys Leu Ile Pro Val Leu Lys Val Val
65                  70                  75                  80 cga ctt gat gaa gag acc act atc gcc cgc gca atc atg ctg gtt aag    288
Arg Leu Asp Glu Glu Thr Thr Ile Ala Arg Ala Ile Met Leu Val Lys
                85                  90                  95 gtc tct gcg gac agc acc aac cgt ccg cag atc gtc gac gcc gcg aac    336
Val Ser Ala Asp Ser Thr Asn Arg Pro Gln Ile Val Asp Ala Ala Asn
            100                 105                 110 atc ttc cgc gcc cga gtc gtc gac gtg gct cca gac tct gtg gtt att    384
Ile Phe Arg Ala Arg Val Val Asp Val Ala Pro Asp Ser Val Val Ile
        115                 120                 125 gaa tcc aca ggc acc cca ggc aag ctc cgc gca ctg ctt gac gtg atg    432
Glu Ser Thr Gly Thr Pro Gly Lys Leu Arg Ala Leu Leu Asp Val Met
    130                 135                 140 gaa cca tcc gga atc gcg gaa ctg atc caa tcc gga cag att gca ctc    480
Glu Pro Ser Gly Ile Ala Glu Leu Ile Gln Ser Gly Gln Ile Ala Leu
145                 150                 155                 160 aac cgc ggt ccg aag acc atg gct ccg gcc aag atc taa                519
Asn Arg Gly Pro Lys Thr Met Ala Pro Ala Lys Ile
                165                 170

<210> SEQ ID NO 4
<211> LENGTH: 172
<212> TYPE: PRT
<213> ORGANISM: Artificial Sequence
<220> FEATURE:
<223> OTHER INFORMATION: Synthetic Construct

<400> SEQUENCE: 4

Met Ala Asn Ser Asp Val Thr Arg His Ile Leu Ser Val Leu Val Gln
1               5                   10                  15
```

Asp Val Asp Gly Asp Phe Ser Arg Val Ser Gly Met Phe Thr Arg Arg
            20                  25                  30

Ala Phe Asn Leu Val Ser Leu Val Ser Ala Lys Thr Glu Thr His Gly
        35                  40                  45

Ile Asn Arg Ile Thr Val Val Val Asp Ala Asp Glu Leu Asn Ile Glu
    50                  55                  60

Gln Ile Thr Lys Gln Leu Asn Lys Leu Ile Pro Val Leu Lys Val Val
65                  70                  75                  80

Arg Leu Asp Glu Glu Thr Thr Ile Ala Arg Ala Ile Met Leu Val Lys
                85                  90                  95

Val Ser Ala Asp Ser Thr Asn Arg Pro Gln Ile Val Asp Ala Ala Asn
            100                 105                 110

Ile Phe Arg Ala Arg Val Val Asp Val Ala Pro Asp Ser Val Val Ile
        115                 120                 125

Glu Ser Thr Gly Thr Pro Gly Lys Leu Arg Ala Leu Leu Asp Val Met
    130                 135                 140

Glu Pro Ser Gly Ile Ala Glu Leu Ile Gln Ser Gly Gln Ile Ala Leu
145                 150                 155                 160

Asn Arg Gly Pro Lys Thr Met Ala Pro Ala Lys Ile
                165                 170

<210> SEQ ID NO 5
<211> LENGTH: 17
<212> TYPE: DNA
<213> ORGANISM: Artificial Sequence
<220> FEATURE:
<223> OTHER INFORMATION: Synthetic DNA

<400> SEQUENCE: 5
gcggaggaag tactgcc                                                  17

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA

<400> SEQUENCE: 6
caatcagatt aattgctgtt ta                                            22

<210> SEQ ID NO 7
<211> LENGTH: 26
<212> TYPE: DNA
<213> ORGANISM: Artificial Sequence
<220> FEATURE:
<223> OTHER INFORMATION: Synthetic DNA

<400> SEQUENCE: 7
ggacgtagac ggtgacattt cccgcg                                        26

<210> SEQ ID NO 8
<211> LENGTH: 19
<212> TYPE: DNA
<213> ORGANISM: Artificial Sequence
<220> FEATURE:
<223> OTHER INFORMATION: Synthetic DNA

```
<400> SEQUENCE: 8
gtttagaact tggccggag                                                    19

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
gatcctgccg acattcacga                                                   20

<210> SEQ ID NO 10
<211> LENGTH: 57
<212> TYPE: PRT
<213> ORGANISM: Corynebacterium glutamicum

<400> SEQUENCE: 10

Met Ala Asn Ser Asp Val Thr Arg His Ile Leu Ser Val Leu Val Gln
1               5                   10                  15

Asp Val Asp Gly Ile Ile Ser Arg Val Ser Gly Met Phe Thr Arg Arg
            20                  25                  30

Ala Phe Asn Leu Val Ser Leu Val Ser Ala Lys Thr Glu Thr His Gly
        35                  40                  45

Ile Asn Arg Ile Thr Val Val Val Asp
    50                  55

<210> SEQ ID NO 11
<211> LENGTH: 53
<212> TYPE: PRT
<213> ORGANISM: S. cinnamonensis

<400> SEQUENCE: 11

Met Ser Thr Lys His Thr Leu Ser Val Leu Val Glu Asn Lys Pro Gly
1               5                   10                  15

Val Leu Ala Arg Ile Thr Ala Leu Phe Ser Arg Arg Gly Phe Asn Ile
            20                  25                  30

Asp Ser Leu Ala Val Gly Val Thr Glu His Pro Asp Ile Ser Arg Ile
        35                  40                  45

Thr Ile Val Val Asn
    50

<210> SEQ ID NO 12
<211> LENGTH: 57
<212> TYPE: PRT
<213> ORGANISM: Escherichia Coli

<400> SEQUENCE: 12

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Ile Gln Asp Ser Asp
        35                  40                  45

Lys Ser His Ile Trp Leu Leu Val Asn
    50                  55
```

FEEDBACK RESISTANT ACETOHYDROXY ACID SYNTHETHASE MUTANTS

The present invention is directed to specific nucleic acids and polypeptides coded by these nucleic acids as well as their application. The polypeptides of the present invention serve to improve the production of branched-chain amino acids by fermentation.

In particular, the present invention provides nucleotide sequences coding for acetohydroxy acid synthetase (AHAS) mutants, the mutated enzymes themselves and a process for the fermentative production of branched-chain amino acids using these enzymes in specific hosts in which genes which code for the modified acetohydroxy acid synthetase (AHAS) are expressed.

It is known that amino acid may be produced by fermentation of strains of coryneform bacteria, in particular *Corynebacterium glutamicum*. Due to their great significance, efforts are constantly being made to improve the production process. Improvements to the process may relate to measures concerning fermentation technology, for example stirring and oxygen supply, or to the composition, of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the isoleucine analogue isoleucine hydroxyamate (Kisumi M, Komatsubara S, Sugiura, M, Chibata I (1972) Journal of Bacteriology 110: 761-763), the valine analogue 2-thiazolealanine (Tsuchida T, Yoshinanga F, Kubota K, Momose H (1975) Agricultural and Biological Chemistry, Japan 39: 1319-1322) or the leucine analogue α-aminobutyrates (Ambe-Ono Ono Y, Sato K, Totsuka X, Yoshihara Y, Nakamori S (1996) Bioscience Biotechnology Biochemistry 60: 1386-1387) or which are auxotrophic for regulatorily significant metabolites and produce e.g. branched-chain amino acids (Tsuchida T, Yoshinaga F, Kubota K, Momose H, Okumura S (1975) Agricultural and Biological Chemistry; Nakayama K, Kitada S, Kinoshita S (1961) Journal of General and Applied Microbiology, Japan 7: 52-69; Nakayama K, Kitada S, Sato Z, Kinoshita (191) Journal of General and Applied Microbiology, Japan 7: 41-51).

For some years, the methods of recombinant DNA technology have also been used for strain improvement of strains of *Corynebacterium* which produce branched-chain amino acids by amplifying individual biosynthesis genes for branched-chain amino acids and investigating the effect on their production. Review articles on this subject may be found inter alia in Kinoshita ("Glutamic Acid Bacteria", in: Biology of Industrial Microorganisms, Demain and Solomon (Eds.), Benjamin Cummings, London, UK, 1985, 115-142), Hilliger (BioTec 2, 40-44 (1991)), Eggeling (Amino Acids 6:261-272 (1994)), Jetten and Sinskey (Critical Reviews in Biotechnology 15, 73-103 (1995)), Sahm et al. (Annuals of the New York Academy of Science 782, 25-39 (1996)), and Eggeling et al., Journal of Biotechnology 56: 168-180 (1997)).

Among others the branched-chain amino acids L-isoleucine, L-valine and L-leucine are used in pharmaceutical industry, in human-medicine and in animal nutrition. One of the key enzymes of the synthesis of all three amino acids in bacteria is the acetohydroxy acid synthetase (AHAS). It catalyses-two reactions giving rise to precursors of the three amino acids.

In valine and leucine biosynthesis pathway, the substrate for AHAS is pyruvate. AHAS catalyses the decarboxylation of pyruvate and its condensation with the second molecule of pyruvate to produce acetolactate. In the isoleucine pathway, AHAS catalyses reaction of pyruvate and 2-ketobutyrate producing acetohydroxy butyrate. In *Escherichia coli* strains, as much as three AHAS isoenzymes exist. Activity of the isoenzymes is inhibited by combinations of amino acids, from which the inhibition by valine is the strongest (De Felice, M., Levinthal, M., Iaccarino, M., Guardiola, J., 1979. Growth inhibition as a consequence of antagonism between related amino acids: effect of valine in *Escherichia coli* K12. Microbiol Rev 43, 4258). AHAS I, coded by the genes ilvBN, is inhibited by valine and isoleucine, AHAS II, coded by ilvGM is valine resistant and AHAS III, coded by ilvIH is inhibited by valine and isoleucine. In all cases the enzyme consists of 2 subunits. In AHAS I and AHAS III the small regulatory subunits coded by the genes ilvN and ilvH, respectively, are responsible for the inhibition.

In contrast to *E. coli*, ilvBM codes for the only AHAS in *C. glutamicum* (Keilhauer, C., Eggeling, L., Sahm, H., 1993. Isoleucine synthesis in *Corynebacterium glutamicum*: molecular analysis of the ilvB-ilvN-ilvC operon. J. Bacteriol. 175, 5595-5603). Activity of the *C. glutamicum* enzyme is inhibited by valine, leucine and isoleucine (Eggeling, I., Cordes, C., Eggeling, L., Sahm, H., 1987. Regulation of acetohydroxy acid synthetase in *Corynebacterium glutamicum* during fermentation of alfa-ketobutyrate to L-isoleucine. Appl Microbiol Biotechnol 25, 346-351). Expression of the gene cluster ilvBNC is also regulated by these three amino acids through the transcriptional attenuation (Morbach, S., Junger, C., Sahm, H., Eggeling, L., 2000. Attenuation control of ilvBNC in *Corynebacterium glutamicum*: evidence of leader peptide formation without the presence of a ribosome binding site. J Biosci Bioeng 90, 501-507).

In *Corynebacterium glutamicum* no mutations deregulating the AHAS activity has been described on molecular level until now.

The object of the present invention was to provide a modified acetohydroxy acid synthetase (AHAS). In particular the AHAS of the present invention shall be less prone to inhibition by amino acids just produced.

This goal is met according to the following embodiments. Embodiment 1 is directed to specific nucleic acids which code for a polypeptide comprising envisaged features. Embodiment 2 embraces the polypeptides themselves. Embodiments 3 and 4 disclose hosts comprising the nucleic acids of the invention or special primers or probes for their production via PCR. Moreover, embodiment 5 specifies a process for the production of further improved polypeptides of the inventions, whereas claim 6 protects the thus produced polypeptides and nucleic acids, respectively. Embodiments 7 and 8 are directed to special uses and embodiment 9 embraces a process for the production of amino acids. Likewise embodiments 10 and 11 provide special vectors and microorganisms.

Figure 1:
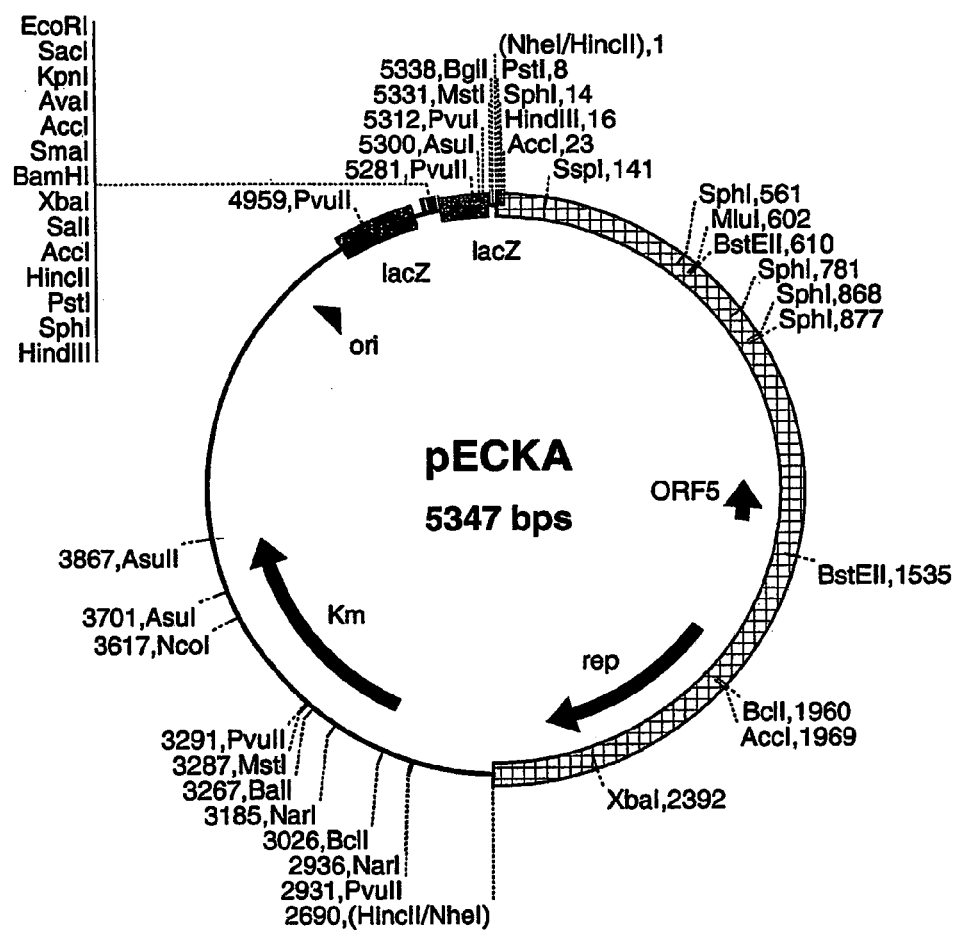
FIG. 1 depicts plasmid pECKA.

By providing isolated nucleic acid sequences coding for a polypeptide having acetohydroxy acid synthetase (AHAS) activity selected from the group consisting of:

a) a nucleic acid sequence according to SEQ. ID No: 1 or SEQ. ID NO: 3;
b) a nucleic acid sequence comprising in position 21 and 22 a base triplet coding for Asp and Phe, respectively;
c) a nucleic acid sequence hybridising under stringent conditions with those of a) or b);
d) a nucleic acid sequence having a homology of at least 70% with those of a) or b);
e) a nucleic acid coding for a polypeptide having at least 80% homology on amino acid level with the polypeptide coded by a) or b);
f) a nucleic acid coding for a polypeptide with improved activity and/or selectivity and/or stability as compared with the polypeptide coded by a) or b); prepared by
  i) mutagenesis of a nucleic acid of a) or b),
  ii) ligating the nucleic acid sequence obtainable from i) into a suitable vector followed by transformation into a suitable expression system and
  iii) expression and detection of the critical polypeptide with improved activity and/or selectivity and/or stability;
g) a nucleic acid sequence containing at least 15 successive bases of the nucleic acid sequences of a)-f), the obstacles presented above and known from the prior art have surprisingly been overcome in a notwithstandingly superior fashion. The nucleic acids of the invention encode polypeptides having a decreased amino acid feedback inhibition action compared to the wild type enzyme.

The procedure to improve the nucleic acids according to the invention or the polypeptides coded by them using the methods of mutagenesis is sufficiently well-known to a person skilled in the art. Suitable methods of mutagenesis are all the methods available for this purpose to a person, skilled in the art. In particular these include saturation mutagenesis, random mutagenesis, in vitro recombination methods and site-directed mutagenesis (Eigen, M. and Gardiner, W., Evolutionary molecular engineering based on RNA replication, *Pure Appl. Chem.* 1984, 56, 967-978; Chen, K. and Arnold, F., Enzyme engineering for non-aqueous solvents: random mutagenesis to enhance activity of subtilisin E in polar organic media. *Bio/Technology* 1991, 9, 1073-1077; Horwitz, M. and Loeb, L., Promoters Selected From Random DNA-Sequences, *Proc Natl Acad Sci USA* 83, 1986, 7405-7409; Dube, D. and L. Loeb, Mutants Generated By The Insertion Of Random Oligonucleotides Into The Active-Site Of The Beta-Lactamase Gene, *Biochemistry* 1989, 28, 5703-5707; Stemmer, P. C., Rapid evolution of a protein in vitro by DNA shuffling, *Nature,* 1994, 370, 389-391 and Stemmer, P. C., DNA shuffling by random fragmentation and reassembly: In vitro recombination for molecular evolution. *Proc Natl Acad Sci USA* 91, 1994, 10747-10751).

The new nucleic acid sequences obtained are cloned in a host organism using common methods cited below, and the polypeptides expressed in this way are detected and then isolated using suitable screening methods. For the purposes of detection, all the possible detection reactions for the molecules formed with this polypeptide are basically suitable. In particular, a photometric tests via the compounds formed (like e.g. acetolactate) or consumed, HPLC or GC methods can be used here to detect the amino acids formed. In addition, to detect new polypeptides modified by means of genetic engineering techniques, gel electrophoretic methods of detection or methods of detection using antibodies are also suitable.

As mentioned above, the invention also covers nucleic acid sequences which hybridise under stringent conditions with the single-strand nucleic acid sequences according to the invention or single-strand nucleic acid sequences which are complementary thereto.

The expression "under stringent conditions" is to be understood here in the same way as is described in Sambrook et al. (Sambrook, J.; Fritsch, E. F. and Maniatis, T. (1989), Molecular cloning: a laboratory manual, $2^{nd}$ ed., Cold Spring Harbor Laboratory Press, New York). Stringent hybridisation in accordance with the present invention is preferably present when, after growing for one hour with 1×SSC (150 mM sodium chloride, 15 mM sodium citrate, pH 7.0) and 0.1% SDS (sodium dodecylsulfate) at 50° C., preferably at 55° C., more preferably at 62° C. and most preferably at 68° C. and more preferably for one hour with 0.2×SSC and 0.1% SDS at 50° C., preferably at 55° C., more preferably at 62° C. and most preferably at 68° C., a positive hybridization signal is still observed.

A second aspect of the present invention are polypeptides selected from the group consisting of
a) a polypeptide coded by a nucleic acid sequence according to claim 1;
b) a polypeptide having a sequence in accordance with SEQ. ID NO: 2 or SEQ. ID NO: 4;
c) a polypeptide which is at least 84% homologous to a polypeptide with SEQ. ID NO: 2 or SEQ: ID NO. 4, without the activity and/or selectivity and/or stability of the polypeptide being substantially reduced as compared with the polypeptide with SEQ. ID NO: 2 or SEQ. ID NO: 4, which may serve as modified AHAS-enzymes in the biopathway in the production of branched-chain amino acids, in particular valine, leucine and isoleucine, by fermentation. Theses enzymes, as already mentioned, posses less feedback inhibition, hence, leading to the possibility to generate higher concentrations of amino acids in the fermentation broth without having adverse inhibition effects.

In a third aspect the present invention is concerned with plasmids, vectors, micro-organisms comprising one or more of the nucleic acid sequences of the invention. Suitable plasmids or vectors are in principle all embodiments which are available to a person skilled in the art for this purpose. These types of plasmids and vectors can be found e.g. in Studier et al. (Studier, W. F.; Rosenberg A. H.; Dunn J. J.; Dubendroff J. W.; Use of the T7 RNA polymerase to direct expression of cloned genes, *Methods Enzymol.* 1990, 185, 61-89) or in company brochures issued by Novagen, Promega, New England Biolabs, Clontech or, Gibco BRL. Other preferred plasmids and vectors can be found in: Glover, D. M. (1985), DNA cloning: a practical approach, Vol. I-III, IRL Press Ltd., Oxford; Rodriguez, R. L. and Denhardt, D. T (eds) (1988), Vectors: a survey of molecular cloning vectors and their uses, 179-204, Butterworth, Stoneham; Goeddel, D. V., Systems for heterologous gene expression, *Methods Enzymol.* 1990, 185, 3-7; Sambrook, J.; Fritsch, E. F. and Maniatis, T. (1989), Molecular cloning: a laboratory manual, $2^{nd}$ ed., Cold Spring Harbor Laboratory Press, New York.

Figure 2:
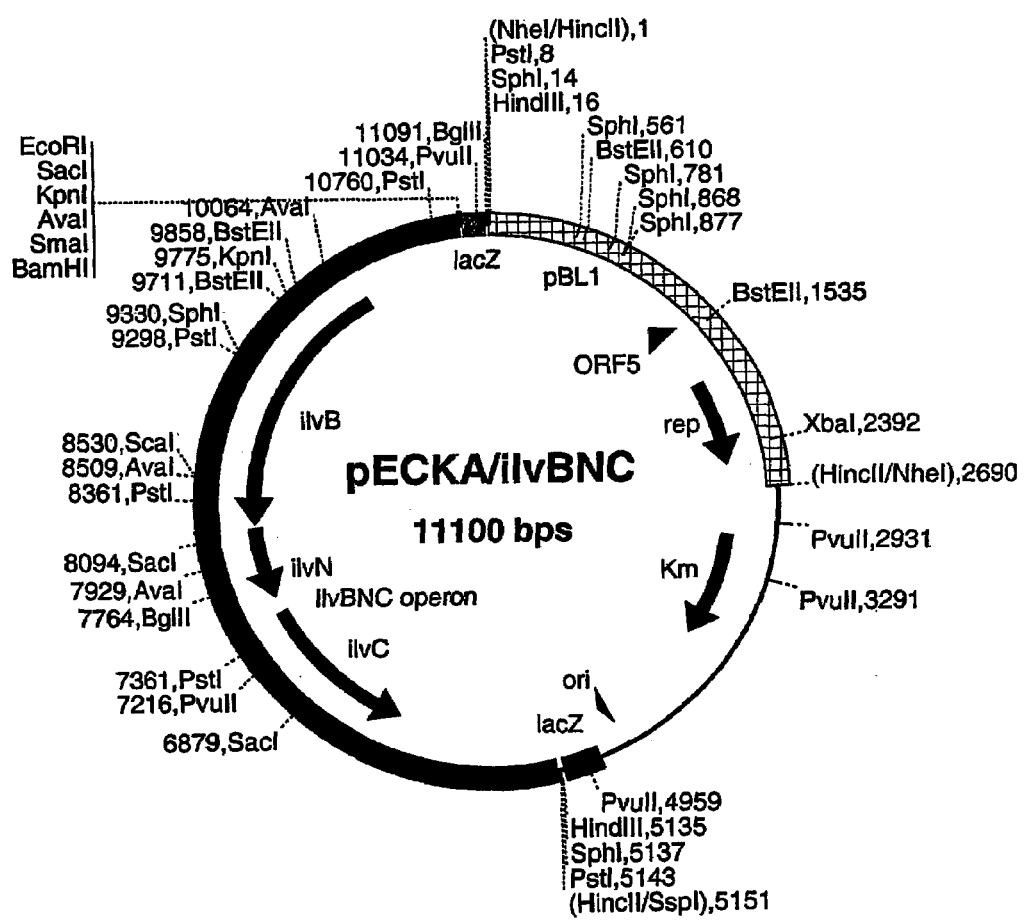
FIG. 2 depicts plasmid pECKA/ilvBNC.

Plasmids with which the gene constructs containing nucleic acids according to the invention can be cloned in a very preferred manner in the host organism are those of FIG. 1 and FIG. 2.

Likewise, the invention also provides microorganisms containing one or more of the nucleic acid sequences according to the invention.

The micro-organism in which the plasmids which contain the nucleic acid sequences according to the invention are cloned may be used to multiply and obtain a sufficient amount of the recombinant enzyme. The processes used for this purpose are well-known to a person skilled in the art (Sambrook, J.; Fritsch, E. F. and Maniatis, T. (1989), Molecular cloning: a laboratory manual, 2$^{nd}$ ed., Cold Spring Harbor Laboratory Press, New York). Micro-organisms which may be referred to are in principle all organisms known to a person skilled in the art which are suitable for this purpose such as e.g. yeasts such as *Hansenula polymorpha*, *Pichia* sp., *Saccharomyces cerevisiae*, prokaryotes, *E. coli*, *Bacillus subtilis* or eukaryontes, such as mammal cells, insect cells. Strains of *E. coli* are preferably used for this purpose. The following are very particularly preferred: *E. coli* XL1 Blue, NM 522, JM101, JM109, JM105,RR1, DH5(X, TOP 10⁻ or HB101. Plasmids with which the gene construct containing the nucleic acid according to the invention is preferably cloned, in the host organism are mentioned above.

Preferred micro-organisms, provided by the present invention, may produce branched-chain amino acids from glucose, sucrose, lactose, mannose, fructose, maltose, molasses, starch, cellulose or from glycerol and ethanol. The micro-organisms may comprise representatives of the coryneform bacteria in particular of the genus *Corynebacterium*. Within the genus *Corynebacterium*, *Corynebacterium glutamicum* may in particular be mentioned, which is known in specialist circles for its ability to produce enantiomerically enriched amino acids, preferably L-amino acids.

Suitable strains of the genus *Corynebacterium*, in particular of the species *Corynebacterium glutamicum*, are in particular the known wild type strains

*Corynebacterium glutamicum* ATCC13032
*Brevibacterium flavum* ATCC14067
*Brevibacterium lactofermentum* ATCC13869 and
*Brevibacterium divaricatum* ATCC14020 and branched-chain amino acid producing mutants or strains produced therefrom, such as for example the isoleucine producing strains
*Corynebacterium glutamicum* ATCC14309
*Corynebacterium glutamicum* ATCC14310
*Corynebacterium gutamicum* ATCC14311
*Corynebacterium glutamicum* ATCC15168
*Corynebacterium ammoniagenes* ATCC 6871, such as for example the leucine producing strains
*Corynebacterium glutamicum* ATCC 21885
*Brevibacterium flavum* ATCC 21889 or such as for example the valine producing strains
*Corynebacterium glutamicum* DSM 12455
*Corynebacterium glutamicum* FERM-P 9325
*Brevibacterium lactofermentum* FERM-P 9324
*Brevibacterium lactofermentum* FERM-BP 1763.

The nucleic acid sequences of the present invention may be overexpressed in a suitable host. Overexpression may be achieved by increasing the copy number of the corresponding genes or by mutating the promoter and regulation region or the ribosome-binding site located upstream from the structural gene. Expression cassettes incorporated upstream from the structural gene act in the same manner. It is additionally possible to increase expression during the fermentative production of branched-chain amino acids by inducible promoters. Expression is also improved by measures to extend the lifetime of the mRNA. Enzyme activity is moreover amplified by preventing degradation of the enzyme protein. The genes or gene constructs may either be present in plasmids in a variable copy number or be integrated in the chromosome and amplified. Alternatively, overexpression of the genes concerned may also be achieved by modifying the composition of the nutrient media and culture conditions. For further guidance in this instance it is referred to U.S. Ser. No. 09/471,803 or its equivalent DE19951708.

Primers for preparing—by means of PCR—or hybridisation probes for detecting the nucleic acid sequences of the invention are a next topic of the present invention. Nucleic acid sequences according to the invention are suitable as hybridisation probes for RNA, cDNA and DNA in order to isolate full length cDNA which code for AHAS proteins and to isolate such cDNA or genes, the sequence of which exhibits a high level of similarity with that of the present invention.

Nucleic acid sequences according to the invention are furthermore suitable as primers, with the assistance of which, using all types of polymerase chain reaction (PCR), DNA of genes which code for AHAS proteins may be generated. Sense and antisense primers coding for the corresponding amino acid sequences, or complementary DNA sequences, are included. Suitable primers may be obtained in principle by processes known to a person skilled in the art. Designing the primers according to the invention is performed by comparison with known DNA sequences or by translating the amino acid sequences detected by eye in the preferred codon of the organism under consideration (e.g. for *Streptomyces*: Wright F. and Bibb M. J. (1992), Codon usage in the G+C-rich *Streptomyces genome*, Gene 113, 55-65). Common features in the amino acid sequence of proteins from so-called superfamilies are also of use in this regard (Firestine, S. M.; Nixon, A. E.; Benkovic, S. J. (1996), Threading your way to protein function, Chem. Biol. 3, 779-783). Further information on this topic can be found in Gait, M., J. (1984), Oligonucleotide synthesis: a practical approach, IRL Press Ltd., Oxford; Innis, M. A.; Gelfound, D. H.; Sninsky, J. J. and White, T. J. (1990), PCR Protocols: A guide to methods and applications, Academic Press Inc., San Diego. The following primers are extremely preferred:

|  |  | SEQ. ID NO: 5 |
|---|---|---|
| MILVNH: | 5'GCGGAGGAAGTACTGCC 3' | |
|  |  | SEQ. ID NO: 6 |
| MILVND: | 5'CAATCAGATTAATTGCTGTTTA 3' | |
|  |  | SEQ. ID NO: 7 |
| ILVM1: | 5'GGACGTAGACGG(A)TGACA(T)TTTCCCGCG 3' | |
|  |  | SEQ. ID NO: 8 |
| MISBGL: | 5'GTTTAGAACTTGGCCGGAG 3' | |
|  |  | SEQ. ID NO: 9 |
| SILVNH: | 5' GATCCTGCCGACATTCACGA 3' | |

Such nucleic acid sequences acting as probes or primers have at least 30, preferably at least 20, very particularly preferably at least 15 successive nucleic acids in common with those of the invention. Nucleic acid sequences having a length of at least 40 or 50 base pairs are also suitable.

A further embodiment of the present invention is directed to a process for preparing improved rec-polypeptides with acetohydroxy acid synthetase (AHAS) activity starting from nucleic acid sequences in accordance with the invention, characterised in that a) the nucleic acid sequences are subjected to mutagenesis,
b) the nucleic acid sequences obtainable from a) are cloned in a suitable vector and these are transferred into a suitable expression system and
c) the polypeptides with improved activity and/or selectivity and/or stability which are formed are detected and isolated.

The invention also provides rec-polypeptides or nucleic acid sequences coding for these which are obtainable by a process like the one just described.

Preparation of the nucleic acid sequences required to produce the improved rec-polypeptides and their expression in hosts is described supra and accordingly applies here.

The polypeptides and improved rec-polypeptides according to the invention are preferably used to prepare enantiomer-enriched branched-chain amino acids, more preferably valine, leucine and isoleucine.

In addition the nucleic acid sequences and improved nucleic acid sequences may preferentially be used to prepare an branched-chain amino acid producing micro-organism.

A next development of the invention reflects a process for the production of branched-chain amino acids with utilises a polypeptide of the invention.

Moreover vectors pECKA (FIG. 1) or pECKA/ilvBNC (FIG. 2) are embraced by present invention. Furthermore modified micro-organisms like DSM15652, DSM15561 or DSM15650 are enclosed in present invention. They were deposited at the Deutsche Sammlung für Mikroorganismen und Zellkulturen GmbH, Mascheroder Weg 1b, D-38124 Braunschweig, according to the Budapest Treaty on Jun. 4, 2003.

For cloning of the ilvBNC operon containing the mutations in the ilvN gene, the shuttle vector *Escherichia coli-Corynebacterium glutamicum* was constructed. First recognition site for the restriction enzyme BglII was removed from the vector pK19. Then, HindIII/HindII fragment (2.7 kb) of the plasmid pBL1 from *Brevibacterium lactofermentum* was cloned into NheI site of pK19. The resulting plasmid vector pECKA (5.4 kb) replicates in *Escherichia coli* and *Corynebacterium glutamicum*, provides 7 unique cloning sites, kanamycin resistance marker and α-complementation of β-galactosidase for cloning in *E. coli*. The Chromosomal fragment SspI/EcoRI (5.7 kb) (with SspI+BaHI ends) carrying the ilvBNC operon was cloned into the HindII+BamHI-digested vector pECKA to create pECKAilvBNC (11.1 kb).

The natural ScaI/BglII fragment of ilvBNC operon (770 bp) was exchanged with the same fragment containing 3 to 5 base alterations constructed by site-directed mutagenesis. The target for site-directed mutagenesis was the conserved domain of the regulatory subunit coded by ilvN near the N terminus. Mutations were designed by PCR according to the sequences of the *Escherichia coli* and *Streptomyces cinnamonensis* AHAS mutants. Mutations were detected by sequencing.

Plasmid DNA was isolated from *Escherichia coli* and the strain *Corynebacterium glutamicum* ATCC13032ΔilvN was transformed with the plasmids pECKAilvBNC(WT), pECKAiNlvBNC(M8) and pECKAilvBNC(M13). The decrease of inhibition of AHAS by branched-chain amino acids was demonstrated.

"Isolated" means separated from its natural environment.

Optically enriched (enantiomerically enriched, enantiomer enriched) compounds in the context of this invention is understood to mean the presence of >50 mol % of one optical antipode mixed with the other.

The expression nucleic acid sequences is intended to include all types of single-strand or double-strand DNA and also RNA or mixtures of the same.

An improvement in activity and/or selectivity and/or stability means, according to the invention, that the polypeptides are more active and/or more selective and are more stable under the reaction conditions used. Whereas the activity and stability of enzymes for industrial application should naturally be as high as possible, with regard to the selectivity an improvement is referred to either when either the substrate selectivity decreases or the enantioselectivity of the enzymes increases. For the expression not substantially reduced, used in this connection, the same definition applies mutatis mutandis.

The claimed protein sequences and nucleic acid sequences also include, according to the invention, those sequences which have a homology (excluding natural degeneration) of greater than 91%, preferably greater than 92%, 93% or 94%, more preferably greater than 95% or 96% and particularly preferably greater than 97%, 98% or 99% to one of these sequences, provided the mode of action or purpose of such a sequence is retained. The expression "homology" (or identity) as used herein can be defined by the equation $H (\%)=[1-V/X]\times 100$, where H means homology, X is the total number of nucleobases/amino acids in the comparison sequence and V is the number of different nucleobases/amino acids in the sequence being considered with reference to the comparison sequence. In each case the expression nucleic acid sequences which code for, polypeptides includes all sequences which appear to be possible, in accordance with degeneration of the genetic code.

The literature references mentioned in this document are regarded as being included within the disclosure.

EXAMPLES

1. Construction of the Plasmid Vector pECKA

For cloning of the *C. glutamicum* ilvBNC operon containing the mutations in the ilvN gene and for its overexpression, the shuttle vector replicating in *Escherichia coli* and *Corynebacterium glutamicum* was constructed. First, recognition site for the restriction enzyme BglII was removed from the vector pK19 (Pridmore, R. D., 1987. New and versatile cloning vectors with kanamycin-resistance marker. Gene 56, 309-312). The plasmid pK19 was digested by BglII, blunt-ended by Klenow enzyme and religated. After ligation, *E. coli* DH5α cells were transformed with the ligation mixture and transformants containing the resulting plasmid pK19B were selected on agar plates containing kanamycin (20 mg/i). The removal of the BglII site in pK19B was confirmed by the treatment of the isolated plasmid molecule with BglII. (This removal has permitted later subcloning of the fragment carrying the ilvN gene into the newly constructed vector pECKA.) Then, HindIII/HindII fragment (2.7 kb) of the plasmid pBL1 from *Brevibacterium lactofermentum* blunt-ended by the Klenow enzyme was cloned into the blunt-ended NheI site of pK19B. The resulting plasmid vector pECKA. (5.4 kb) replicates in *Escherichia coli* and *Corynebacterium glutamicum*, provides 7 unique cloning sites (HindII, SalI, BamHI, SmaI, AvaI, KpnI, SacI) kanamycin resistance marker and α-complementation of β-galactosidase for cloning in *E. coli*. Its restriction and genetic map is shown in FIG. 1.

2. Cloning of the ilvBNC Operon into the Vector pECKA

The 5.7-kb fragment of *C. glutamicum* chromosome carrying the ilvBNC operon was obtained by digestion of the plasmid pKK5 (Keilhauer, C., Eggeling, L., Sahm, H., 1993. Isoleucine synthesis in *Corynebacterium glutamicum*: molecular analysis of the ilvB-ilvN-ilvC operon. J. Bacteriol. 175, 5595-5603) with the restriction enzymes SspI and BamHI. The fragment was ligated with the HindII+BamHI-digested vector pECKA and the ligation mixture was used for transformation of *E. coli* DH5α. The transformants were selected on the agar plates containing kanamycin (30 mg/l).

The structure of the resulting plasmid pECKAilvBNC (11.1 kb) was confirmed by restriction analysis. The restriction and genetic map of the plasmid pECKAilvBNC is shown in FIG. 2.

3. Design of the Oligonucleotide Primer for Mutagenesis of the ilvN Gene

The known amino acid sequence of the regulatory subunit of AHAS coded by the *C. glutamicum* ilvN gene (GenBank accession number L09232) was aligned with the known amino acid sequences of regulatory subunits of AHAS from *Streptomyces cinnamonensis* (GenBank accession numbers; AF175526) and from *Escherichia coli* (GenBank accession number AE016769, section 15 of the complete genome). Several mutations of *Escherichia coli* and *Streptomyces cinnamonensis* conferring resistance to valine were described (Vyazmensky, M., Sella, C., Barak, Z., Chipman, D. M., 1996. Isolation and characterization of subunits of acetohydroxy acid synthase isozyme III and reconstitution of the holoenzyme. Biochemistry 35, 10339-10346; Kopecký, J., Janata, J., Pospíšil, S., Felsberg, J., Spížek, J., 1999. Mutations in two distinct regions of acetolactate synthase regulatory subunit from *Streptomyces cinnamonensis* result in the lack of sensitivity to end-product inhibition. Biochem Biophys Res Commun 266, 162-166). In some strains displaying this phenotype, a mutation changing amino acid glycine to aspartate at position 20. (in *E. coli* sequence numbering) was found in both *E. coli* and *S. cinnamonensis* at the partially conserved domain near the N-terminus of the protein:

```
C. glutamicum (SEQ. ID NO: 10)
MANSDVTRHILSVLVQDVDGIISRVSGMFTRRAFNLVSLVSAKTETHGIN
RITVVVD S. cinnamonensis (SEQ. ID NO: 11)
MS----TKHTLSVLVENKPGVLARITALFSRRGFNIDSLAVGVTEHPDIS
RITIVVN E. coli (SEQ. ID NO: 12)
MQNTTHDNVILELTVRNHPGVMTHVCGLFARRAFNVEGILCLPIQDSDKS
HIWLLVN
```

We have designed a degenerated oligonucleotide primer ILVNM1 (SEQ. ID NO: 7) for site-directed mutagenesis of the ilvN gene of *C. glutamicum*. This primer may introduce mutations into the ilvN gene at the positions of the nucleotide triplets corresponding to the amino acids glycine, isoleucine and isoleucine at positions 20 to 22 in *C. glutamicum* AHAS regulatory subunit:

```
Primer ILVNM1 (SEQ. ID NO: 7):

17  18  19  20  21  22  23  24
5' G   GAC GTA GAC GGT GAC ATT TCC CGC G 3'
                     A   T
```

The nucleotides altered, comparing to the sequence of the wild type, are shown in bold face. There are two degenerated positions, within triplets 20 and 22 (G or A and A or T, respectively).

4. Site-Directed Mutagenesis of the ilvN Gene

Site-directed mutagenesis of the natural ScaI/BglII fragment of *C. glutamicum* ilvBNC operon (770 bp) was performed using PCR reactions and 4 oligonucleotide primers (Ito, W., Ishiguro, H., Kurosawa, Y., 1991. A general method for introducing a series of mutations into cloned DNA using the polymerase chain reaction. Gene 102, 67-70).

The primers used:

```
MILVNH
5'GCGGAGGAAGTACTGCC 3'              (SEQ. ID NO: 6)

MILVND
5'CAATCAGATTAATTGCTGTTTA 3'         (SEQ. ID NO: 7)

ILVM1
5'GGACGTAGACGGTGACATTTCCCGCG 3'     (SEQ. ID NO: 8)
              A   T

MISBGL
5'GTTTAGAACTTGGCCGGAG 3'            (SEQ. ID NO: 9)
```

First PCR: Using the primers MILVNH and MISBGL the fragment A (786 bp) with altered natural BglII site was amplified. Using the primers ILVMI and MILVND the fragment B (491 bp) with mutations within ilvN gene was amplified. As a template, the plasmid pECKAilvBNC was used. The resulting DNA fragments-were separated in the agarose gel, isolated and purified by precipitation.

Second PCR: Using primers MILVNH-MILVND and template fragments A+B (mixed in a molar ratio 1:1), a mixture of fragment C (803 bp) with mutation in BglII site and fragment D (803 bp) with mutations in the ilvN gene were amplified. This mixture was digested by ScaI and BglII and the resulting fragments were isolated from the agarose gel. The plasmid pECKAilvBNC was digested by the same enzymes providing fragments of 766 bp and 10334 bp and the larger fragment was also isolated from the gel. The isolated fragments were mixed and ligated. The cells of *E. coli* DH5α were transformed by the ligation mixture and transformants were selected on the plates with kanamycin (30 mg/l). In this way, a natural ScaI/BclII chromosomal fragment (766 bp) in the plasmid pECKAilvBNC was exchanged for the same fragment in which ilvN can contain 3 to 5 altered nucleotides.

5. Sequencing of the Mutants of ilvN

Plasmid DNA from the obtained *E. Coli* DH5α clones was isolated and sequenced using the primer SILVNH and automatic sequencer Vistra (Amersham).

Primer SILVNH:

```
5' GATCCTGCCGACATTCACGA 3'   (SEQ. ID NO: 9)
```

Clones with 2 different sequences within the triplets 20 to 22 were isolated:

Clones mutated in the ilvN gene obtained:

| | | Amino acid position | | |
|---|---|---|---|---|
| Mutant | DNA sequence | 20 | 21 | 22 |
| WT | GGAATCATT | Gly | Ile | Ile |
| M8 | GGTGACTTT | Gly | Asp | Phe |
| M13 | GATGACTTT | Asp | Asp | Phe |

The complete ilvN sequences of the mutants M8 and M13 are shown in Seq. 3 and 1, respectively.

6. Transformation of *Corynebacterium glutamicum*

Plasmid DNA was isolated from *Escherichia coli* and the strain *Corynebacterium glutamicum* ATCC13032 ΔilvN was transformed with the plasmids pECKAilvBNC(WT), pECKAilvBNC(M8) and pECKAilvBNC(M13) using the electroporation method (Liebl, W., Bayerl, A., Schein, B., Stillner, U., Schleifer, K. H., 1989. High efficiency electroporation of intact *Corynebacterium glutamicum* cells. FEMS Microbiol. Lett. 53, 299-303). Transformants were selected on the plates with kanamycin (30 mg/l).

7. Measurements of the AHAS Activity and of its Inhibition by Valine, Leucine and Isoleucine Strains *C. glutamicum* ATCC13032 ΔilvN carrying the plasmids pECKAilvBNC(WT), pECKAilvBNC(M8) and pECKAilvBNC(M13) were used for measuring the activity of AHAS. The cells were cultivated in the minimal medium CGXII overnight, harvested by centrifugation and disrupted by sonication. After centrifugation (16000×g, 30 min) AHAS activity was measured in the cell-free extract. The spectrophotometric enzyme assay detects indirectly the reaction product acetolactate (Singh, B. K., Stidham, M. A., Shaner, D. L., 1988. Assay of acetohydroxyacid synthase. Anal Biochem 171, 173-179). The assay involves the conversion of the end product acetolactate to acetoin and the detection of acetoin via the formation of a creatine and naphthol complex.

The results of the enzyme activity measurements are shown in table 1. To test the inhibition of the enzyme by valine, leucine and isoleucine, the three amino acids (10 mM) were separately added into the reaction mixture. The results are shown in table 2 and table 3, respectively.

TABLE 1

AHAS activity

| Strain/plasmid | Specific AHAS activity (nmol acetoin min$^{-1}$ mg$^{-1}$ of protein) |
|---|---|
| *C. glutamicum* ATCC13032 | 33.7 ± 10 |
| *C. glutamicum* ATCC13032 ΔilvN | 0.43 |
| *C. glutamicum* ATCC13032 ΔilvN/ pECKAilvBNC (WT) | 110 ± 40 |
| *C. glutamicum* ATCC13032 ΔilvN/ pECKAilvBNC(M8) | 31.1 ± 0.9 |
| *C. glutamicum* ATCC13032 ΔilvN/ pECKAilvBNC(M13) | 40.9 ± 13 |

TABLE 2

Inhibition of AHAS activity

| Strain/plasmid | — | Val | Leu | Ile |
|---|---|---|---|---|
| *C. glutamicum* ATCC13032 | 33.7 | 16.9 | 20.9 | 21.2 |
| *C. glutamicum* ATCC13032 ΔilvN/ pECKAilvBNC WT | 110 | 61.6 | 71.5 | 68.2 |
| *C. glutamicum* ATCC13032 ΔilvN/ pECKAilvBNC(M8) | 31.1 | 35.1 | 34.8 | 32.7 |
| *C. glutamicum* ATCC13032 ΔilvN/ pECKAilvBNC(M13) | 40.9 | 40.7 | 44.2 | 40.0 |

Specific AHAS activity with 10 mM amino acid (nmol acetoin min$^{-1}$ mg$^{-1}$ of prot.)

TABLE 3

Inhibition of AHAS activity in percentage

| Strain/plasmid | Val | Leu | Ile |
|---|---|---|---|
| *C. glutamicum* ATCC13032 | 50% | 38% | 37% |
| *C. glutamicum* ATCC13032 ΔilvN/ pECKAilvBNC WT | 44% | 35% | 38% |
| *C. glutamicum* ATCC13032 ΔilvN/ pECKAilvBNC(M8) | 0% | 0% | 0% |
| *C. glutamicum* ATCC13032 ΔilvN/pECKAilvBNC(M13) | 0% | 0% | 2.5% |

Inhibition (10 mM amino acid)

The invention claimed is:

1. An isolated nucleic acid sequence encoding a polypeptide having acetohydroxy acid synthetase (AHAS) activity and encoding a polypeptide that does not contain the sequence Gly Ile Ile at the positions corresponding to residues 20-22 of SEQ ID NO: 2 comprising:
   (a) SEQ ID NO: 1,
   (b) SEQ ID NO: 3, or
   (c) a polynucleotide sequence that is at least 95% homologous to SEQ ID NO: 1 or 3;
   wherein said polynucleotide sequence does not encode a protein comprising the sequence Gly Ile Ile at the positions corresponding to residues 20-22 of SEQ ID NO: 2.

2. The isolated nucleic acid sequence of claim 1, which comprises (a) SEQ ID NO: 1 or SEQ ID NO: 3.

3. The isolated nucleic acid sequence of claim 1, which comprises (c) a polynucleotide sequence that is at least 95% homologous to SEQ ID NO: 1 or SEQ ID NO: 3.

4. The isolated nucleic acid sequence of claim 1, which is at least 98% homologous to SEQ ID NO: 1 or SEQ ID NO: 3.

5. The isolated nucleic acid sequence of claim 1, which encodes a polypeptide that is at least 84% homologous with the amino acid sequence of SEQ ID NO: 2 or SEQ ID NO: 4.

6. The isolated nucleic acid sequence of claim 1, which contains a codon encoding Asp and Phe, respectively, in the position corresponding to amino acids 21 and 22 in SEQ ID NO: 2 or SEQ ID NO: 4.

7. A vector comprising the isolated polynucleotide sequence of claim 1.

8. The vector of claim 7 that is Vector pECKA or pECKA/ilvBNC.

9. A host cell comprising the vector of claim 7.

10. The host cell of claim 9 that is *Escherichia coli*.

11. The host cell of claim 9 that is *Bacillus subtilis*.

12. The host cell of claim 9 that is *Corynebacterium* or *Brevibacterium*.

13. The host cell of claim 9, which is a yeast.

14. The host cell of claim 9 that is a mammalian or insect cell.

15. The host cell of claim 9 that has been deposited under accession number DSM15652, DSM15651, or DSM15650.

16. A method for making a polypeptide having acetohydroxy acid synthetase (AHAS) activity comprising culturing or growing the host cell of claim 9 in a medium suitable for expression of said polynucleotide and recovering a polypeptide having acetohydroxy acid synthetase (AHAS) activity.

* * * * *